(12) United States Patent
Pazenok

(10) Patent No.: US 6,969,768 B2
(45) Date of Patent: Nov. 29, 2005

(54) PREPARATION OF 4-HALOALKYLNICOTINIC ESTERS

(75) Inventor: Sergiy Pazenok, Kelkheim (DE)

(73) Assignee: Bayer CropScience GmbH, Frankfurt (DE)

( * ) Notice: Subject to any disclaimer, the term of this patent is extended or adjusted under 35 U.S.C. 154(b) by 80 days.

(21) Appl. No.: 10/238,463

(22) Filed: Sep. 9, 2002

(65) Prior Publication Data

US 2003/0083502 A1 May 1, 2003

(30) Foreign Application Priority Data

Sep. 11, 2001 (DE) .......................... 101 44 410

(51) Int. Cl.[7] .................. C07D 211/60; C07D 211/72; C07C 207/00
(52) U.S. Cl. ................. 546/227; 568/307; 546/341; 546/296; 546/298
(58) Field of Search ................ 546/341, 227, 546/296, 298; 568/307

(56) References Cited

U.S. PATENT DOCUMENTS

| | | | |
|---|---|---|---|
| 5,360,806 A | * 11/1994 | Toki et al. .................. | 514/318 |
| 5,708,175 A | * 1/1998 | Koyanagi et al. ........... | 546/250 |
| 6,239,160 B1 | 5/2001 | Tiebes et al. | |

FOREIGN PATENT DOCUMENTS

| | | |
|---|---|---|
| DE | 100 14 006 | 9/2001 |
| EP | 0580374 A | 1/1994 |
| EP | 0 580 374 A1 | 1/1994 |
| EP | 0744400 A | 11/1996 |
| EP | 0 744 400 A2 | 11/1996 |
| WO | WO 98/57969 | 12/1998 |

OTHER PUBLICATIONS

Okada et al, "A Facile and Convenient Synthetic Method for 3–Trifluoroacetyl–Pyrroles", (1992), vol. 34, No. 7, pp. 1435–1441, also referred to as XP00019621.

Okada et al, "A Facile and Convenient Synthetic Method for N–β–Trifluoroacetylvinyl Amino Acid Esters, α–Aminoaccetophenones and Aminoacctonitriles as Potentially Useful Precursors of Fluorine–containing Pyrroles", (1992), pp. 533–535, also referred to as XP000196319.

\* cited by examiner

*Primary Examiner*—Cecilia J. Tsang
*Assistant Examiner*—Binta Robinson
(74) *Attorney, Agent, or Firm*—Frommer Lawrence & Haug LLP

(57) ABSTRACT

A process for preparing 4-haloalkylnicotinic esters of the formula (I),

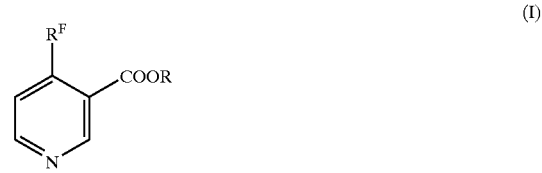

(I)

where
$R^F$ is $(C_1-C_4)$-haloalkyl and
R is $(C_1-C_6)$-alkyl;
which comprises
a) reacting an aminoketone of the formula (II),

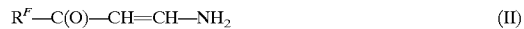

$$R^F-C(O)-CH=CH-NH_2 \quad (II)$$

in a condensation reaction under reduced pressure with a compound of the formulae (III) to (V),

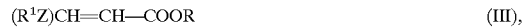
$$(R^1Z)CH=CH-COOR \quad (III),$$

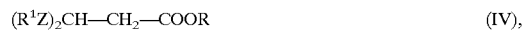

$$(R^1Z)_2CH-CH_2-COOR \quad (IV),$$

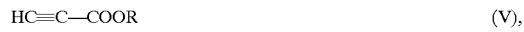

$$HC\equiv C-COOR \quad (V),$$

where
$R^1$ is $(C_1-C_6)$-alkyl and
Z is O, S, $NR^1$ or C(O)O,
to give a compound of the formulae (VI) and/or (VII),

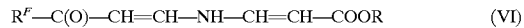
$$R^F-C(O)-CH=CH-NH-CH=CH-COOR \quad (VI)$$

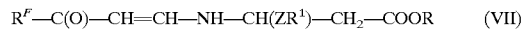

$$R^F-C(O)-CH=CH-NH-CH(ZR^1)-CH_2-COOR \quad (VII)$$

b) and subjecting the reaction product to a ring closure reaction.

9 Claims, No Drawings

PREPARATION OF 4-HALOALKYLNICOTINIC ESTERS

The invention relates to a process for preparing 4-haloalkyl-3-pyridinecarboxylic esters (4-haloalkylnicotinic esters) and to further reaction thereof to give haloalkylnicotinic acid derivatives effective as insecticides.

4-Haloalkylnicotinamides are useful starting materials for preparing pesticides as described, for example, in WO-A 98/57 969, EP-A 0 580 374 and DE-A 100 14 006.

These compounds may be prepared in two steps from 4-haloalkylnicotinic acids, whose preparation by the ring closure of methyl 3-(4,4,4-trifluoro-3-oxo-1-butenylamino) acrylate using NaOMe is described, for example, in EP-A 0 744 400.

Surprisingly, a simple process for preparing methyl 4-haloalkylnicotinates (I) has now been found by which 4-haloalkylnicotinamide can be obtained in only one step by ammonolysis.

The invention accordingly provides a process for preparing 4-haloalkylnicotic esters (I),

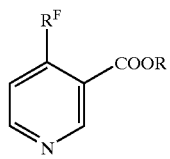
(I)

where
$R^F$ is $(C_1-C_4)$-haloalkyl and
R is $(C_1-C_6)$-alkyl;
which comprises
a) reacting an aminoketone of the formula (II), $R^F$—C(O)—CH=CH—NH$_2$   (II)

where $R^F$ is as defined above,
in a condensation reaction under reduced pressure with a compound of the formulae (III) to (V), $(R^1Z)CH=CH—COOR$   (III), $(R^1Z)_2CH—CH_2—COOR$   (IV),

HC≡C—COOR   (V), where R, $R^1$ are identical or different $(C_1-C_6)$-alkyl and each Z, which may be identical or different, is selected from O, S, $NR^1$ and C(O)O,
to give a compound of the formula (VI) and/or (VII), $R^F$—C(O)—CH=CH—NH—CH=CH—COOR   (VI)

$R^F$—C(O)—CH=CH—NH—CH(ZR$^1$)—CH$_2$—COOR   (VII)

where $R^F$, R, $R^1$ and Z are each as defined above,
and subjecting the reaction product
b) to a ring closure reaction.

Surprisingly the process according to the invention leads to 4-(haloalkyl)nicotinic esters, in contrast, for example, to that described in EP-A 0 744 400, where the ring closure reaction results in the acid or a salt.

The invention also provides a process for preparing compounds of the formulae (VI) and/or (VII), which comprises reacting a compound of the formula (II), $R^F$—C(O)—CH=CH—NH$_2$   (II)

in a condensation reaction under reduced pressure with a compound of the formulae (III) to (V)

$(R^1Z)CH=CH—COOR$   (III)

$(R^1Z)_2C—CH_2—COOR$   (IV)

HC≡C—COOR   (V)

where the symbols are each as defined above.

The invention also provides the use of 4-haloalkylnicotinic esters as intermediates for preparing crop protection agents, in particular pesticides such as insecticides.

The invention also provides a process for preparing 4-haloalkylnicotinamides (VIII),

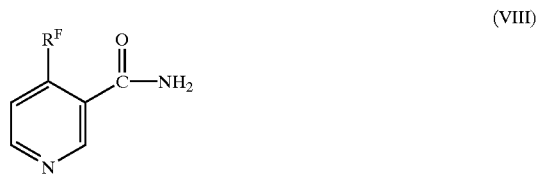
(VIII)

which comprises reacting a 4-haloalkylnicotinic ester (I) obtained by the above process

(I)

with NH$_3$.

A particular economic advantage over the known synthesis from the acid is that no activated acid derivative, for example acyl chloride, is required in the process according to the invention.

Compounds of the formula (II) such as 4-amino-1,1,1-trifluoro-3-buten-2-one are known and may be prepared, for example, as described EP-A 0 744 400, by reacting an acyl halide of the formula (IX), $R^F$—COX   (IX)

where X is a halogen atom, with a compound of the formula (X), $CH_2$=CHOR$^2$   (X)

where $R^2$ is an alkyl group preferably having from 1 to 6 carbon atoms, to give a compound of the formula (XI), $CF_3$—C(O)—CH=CH(OR$^2$)   (XI)

which gives compound (II) by reaction with ammonia.

Compounds of the formulae (III) to (V) are known. They are commercially available or may be prepared by known methods familiar to those skilled in the art, as described, for example, in J. Chem. Soc.; 1969, 406–408; Bull. Soc. Chem. Fr. 1948, 594 and J. Org. Chem.; 29, 1964,1800–1808.

R, $R^1$, $R^2$ are identical or different and are each preferably a linear or branched alkyl group having from 1 to 6, preferably from 1 to 4 carbon atoms, for example, methyl, ethyl, n-propyl, isopropyl, n-butyl or tert-butyl, preferably methyl or ethyl, more preferably methyl.

$R^F$ is $(C_1-C_4)$-haloalkyl, where halo is F, Cl, Br or I, preferably F or Cl. Preference is given to CH$_2$F, CFCl$_2$, $CF_2Cl$, $CF_3$, $C_2F_5$ and $C_3F_7$, more preferably $CF_2Cl$, $C_2F_5$ and $CF_3$, in particular $CF_3$.

Particular preference is given to a compound of the formula (I) where $R^F=CF_3$ and R=methyl.

According to the invention, compound (II) is reacted in a condensation reaction with one or more compounds of the formulae (III) to (V) to give compound (VI) and/or (VII).

The condensation of compound (II) with one or more compounds (III) to (V) and the subsequent ring closure reaction are shown by way of example in the following scheme:

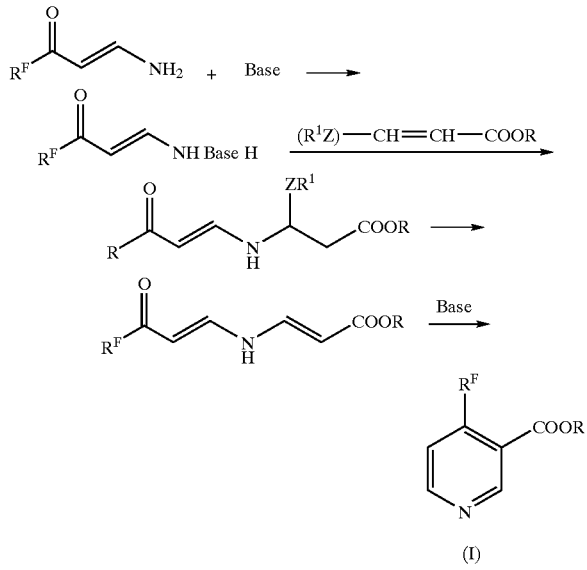

According to the invention, the reaction is carried out under reduced pressure, preferably at a pressure in the range from 5 to 150 mbar, more preferably from 10 to 100 mbar, in particular from 20 to 80 mbar. At the same time, preference is given to distilling off the low-boiling products from the reaction mixture to provide complete conversion of the two reactants. The reduced pressure is advantageously selected in such a way that the boiling point of the detached compound $R^1ZH$, for example, $CH_3OH$, EtOH, or BuOH, is below, preferably from 50 to 10° C. below, the reaction temperature and the boiling point of the solvent is above, preferably from 50 to 80° C., above the reaction temperature.

Depending on the compound used and other reaction conditions, the ratio of the two components (II) and (III) to (V) in the reactions may vary within a wide range.

Customarily, the molar ratio of the components (II):(III) to (V) is 1.0–1.2:1, preferably 1.02–1.06:1.

Depending on the compound used and the other reaction conditions, the reaction temperature may vary within wide limits. In general, the reaction temperature is in the range from −20° C. to +100° C., preferably from 0° C. to +30°C., and the reaction time is customarily from 0.5 to 12 h, preferably from 1 to 6 h. The reaction conditions may vary depending on which compound of the formulae (III) to (V) is used.

Examples of useful bases include alkali metal hydrides such as NaH or KH, alkyllithium compounds such as n-butyllithium or t-butyllithium, alkali metals such as sodium or potassium, alkoxides such as sodium methoxide, sodium ethoxide, potassium methoxide or potassium t-butoxide. Preference is given to alkoxides and alkali metal hydrides, and particular preference to: NaH; NaOMe, NaO$^t$-But and KO$^t$But. For industrial scale applications, preference is given to NaOMe, NaO$^t$But and KO$^t$But. The bases may be used individually or as a mixture. The quantity of base used may vary within wide limits, depending on what kind of compound of the formula (III) is used, which, if any solvent is used and also the further reaction conditions. In general, from 1.0 to 1.2 equivalents of base, preferably from 1.02 to 1.06 equivalents of base, per mole of the compound of the formula (III) are used.

Preference is given to carrying out the reaction in a solvent. The components (III) to (IV) may both be initially charged in the solvent and these solutions reacted together, or one of the components may be initially charged in the solvent and the other component added, or the base is added to a solution of both components.

Preferred solvents include polar, aprotic solvents such as N,N-dimethylformamide, N-methylpyrrolidone (NMP), sulfolanes or acetonitrile and hydrocarbons. Preference is given to polar aprotic solvents, and particular preference to N,N-dimethylformamide (DMF) and NMP. Mixtures of the solvents mentioned may also be used.

The quantity of solvent used may vary within wide limits and depends, for example, on which base, if any, is added. In general, the quantity of solvent used is from 1 to 30, preferably from 4 to 15, parts by weight per part by weight of compound (III).

Compounds of the formula (Ia) are prepared by reacting a compound of the formula (II) with a compound of the formula (IV) in two stages, the first of which involves detaching the $R^1Z$ group to form the compound of the formula (Ib) and then the second stage detaches a further $R^1ZH$ molecule, which leads to the compound of the formula (Ia).

1st stage

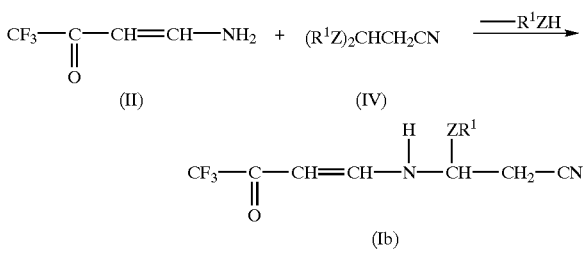

2nd stage

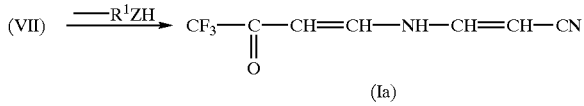

In all reactions, the salts may be used instead of the pure compounds or, depending on the reaction, be obtained.

When the condensation reaction is carried out in the presence of a base which comprises an alkali metal, the compounds (Ia) and (Ib) form alkali metal salts. In such cases, the condensation reaction is followed by a neutralization step using an acid. The workup is effected by known methods familiar to those skilled in the art, such as filtration, washing and drying.

In a preferred embodiment, the process according to the invention is carried out continuously, for example, by passing a mixture of compounds (II), (III) and/or (IV) and base in a solvent under reduced pressure through a heated tubular reactor.

The ring closure reaction of the compounds (VI) and/or (VII) to give compound (I) is preferably effected in a solvent. Preference is given to alcohols, greater preference to primary ($C_1$–$C_6$)-alcohols, even greater preference to methanol and ethanol, in particular methanol. Mixtures of the solvents mentioned may also be used.

The compounds (VI) and/or (VII) may be initially charged in the solvent, or the solvent is added to the reaction mixture.

Depending on the starting compound and the reaction conditions, the quantity of solvent used for the ring closure reaction may vary within wide limits. In general, it is from 1 to 30, preferably from 4 to 15 parts by weight per part by weight of compound (VI) and/or (VII).

The ring closure reaction of the compounds (VI) and/or (VII) is advantageously effected in an alcohol as solvent and in the presence of a preferably weak base to give the intermediates (XII) and/or (XIII). Subsequent acidification gives a compound (I):

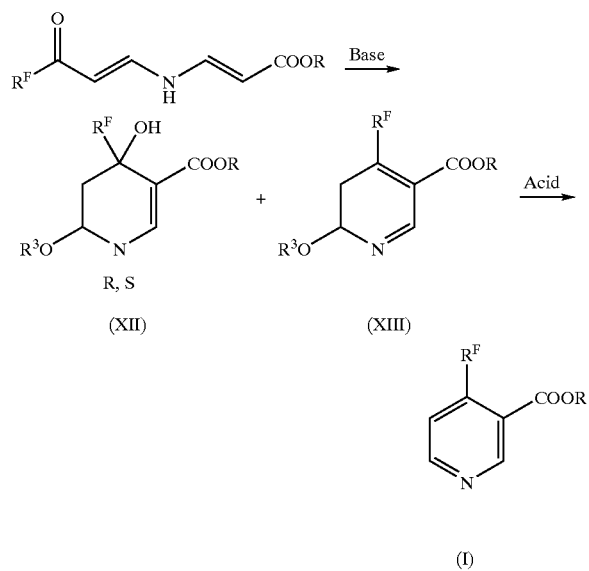

$R^3$ is a preferably straight-chain ($C_1$–$C_6$)-, preferably ($C_1$–$C_4$)-, in particular ($C_1$–$C_2$)-alkyl radical.

Compounds of the formulae (XII) and (XIII) likewise form part of the subject matter of the invention.

Examples of useful bases include alkali metal carbonates, hydrogencarbonates and acetates, such as the appropriate Li, Na, K and Cs salts, and alkali earth metal carbonates and hydrogencarbonates, such as the appropriate Mg and Ca salts.

Preference is given to alkali metal and alkaline earth metal carbonates, hydrogencarbonates and acetates, such as $Li_2CO_3$, $Na_2CO_3$, $NaHCO_3$, $K_2CO_3$, $CaCO_3$ and $MgCO_3$. Particular preference is given to $Li_2CO_3$, $Na_2CO_3$ and $K_2CO_3$, very particular preference to $Li_2CO_3$ and $K_2CO_3$. The two latter bases in particular allow the selectivity of the reaction toward the desired end product (I) to be increased and avoid hydrolysis of the ester.

The bases may be used individually or in a mixture. In general, from 0.05 to 1 equivalent, preferably from 0.1 to 0.8 equivalent of base per mole of compound of the formula (VI) and/or (VII) is used. If desired, the base may be filtered off after the reaction and reused.

The activity and selectivity of the base may be controlled by phase transfer catalysts. Useful phase transfer catalysts are typically crown ethers, cryptands and quaternary ammonium, phosphonium and onium compounds. Examples thereof include 12-crown-4, 15-crown-5, 18-crown-6, dibenzo-18-crown-6, dicyclohexyl-18-crown-6, tetrabutylammonium chloride and bromide, and tetrabutylphosphonium chloride and bromide. Preference is given to 18-crown-6. The phase transfer catalyst is customarily used in a quantity of from 1 to 10, preferably from 1 to 5 mol %, based on the compound (VI) and/or (VII).

The intermediates of the formula (XII) and/or (XIII) may be isolated by customary methods familiar to those skilled in the art, for example, by removing the solvent and washing the residue.

These compounds likewise form part of the subject matter of the invention.

However, preference is given to reaction of the intermediates of the formula (XII) and/or (XIII) without preceding isolation by treating with acid to give compound (I).

For this purpose, preference is given to strong acids such as aqueous or gaseous HCl, HBr, $H_2SO_4$ and $CF_3COOH$. The pH of the reaction mixture is generally adjusted to from 1 to 2, which is customarily achieved by using from 0.1 to 1 equivalent of acid, based on the theoretical quantity of compound (I).

The ester (I) may be converted to the amide (VIII) by known methods familiar to those skilled in the art, as described, for example, in Houben Weyl, Methoden der organischen Chemie.

In a further, preferred variant of the process according to the invention, the synthesis of compounds (I) and (VIII) is carried out in a one-pot reaction, i.e. without the intermediates of the formulae (V), (VI) and/or (XII)/(XIII) being isolated.

The compounds (I) and (VIII) find use, for example, as intermediates in preparing crop protection agents, in particular pesticides such as insecticides.

In particular, they are suitable for further reaction to given compounds as described in WO-A 98/57969, EP-A 0 580 374 and DE 100 14 006.8. These documents, in particular the compounds of the formula (I) in each case and the inventive examples, are hereby expressly incorporated by way of reference.

The invention also provides a process for preparing 4-haloalkylnicotinic acid derivatives effective as insecticides as described in WO-A 98/57969, EP-A 0 580 374 and/or DE 100 14 006.8, which comprises preparing 4-haloalkylnicotinic esters as described above, optionally hydrolyzing and further reacting by the processes described in the cited documents to give the insecticidally active end compounds of each formula (I).

The invention is illustrated by the following nonlimiting examples:

The content of the German Patent Applications 10144410.9, whose priority the present application claims, and the appended abstracts is incorporated herein by reference.

EXAMPLE 1

Isomer Mixture of Methyl 3-(4,4,4-trifluoro-3-oxo-1-butenylamino)acrylate 117 g of potassium tert-butoxide in 700 ml of DMF were initially charged under $N_2$ into a 1 l four-neck flask equipped with a thermometer, KPG stirrer, dropping funnel with bubble counter, descending condenser with cooled (–10° C.) reservoir and vacuum connection, and the solution cooled to 0° C. At this temperature, 142 g of 4-amino-1,1,1-trifluoro-3-buten-2-one were added dropwise within 30 min. After the addition had ended, the solution was stirred for a further 30 min and then 148 g of methyl 3,3-dimethoxypropionate were added dropwise at this temperature. The dropping funnel was removed and the pressure in the system slowly reduced to 20–25 mbar.

The mixture was then stirred for 3–5 h at 30–35° C. and 20–25 mbar vacuum, which simultaneously condensed the low-boiling products (methanol, tert-butanol) and condensed them in the reservoir.

The reaction mixture was added to 1000 g of ice with 40 ml of HCl (d 1.19) at 0–10° C. and adjusted to pH 2–3 with HCl. After 1 h, the precipitate was filtered off, washed with 300 ml of ice-water and the product dried. 205 g (92%) of methyl 3-(4,4,4-trifluoro-3-oxo-1-butenylamino)acrylate were obtained as an isomer mixture of 2 stereoisomers.

EXAMPLE 2
Methyl 4-trifluormethylpyridine-3-carboxylate 19 g (0.1 mol) of methyl 3-(4,4,4-trifluoro-3-oxo-1-butenylamino)acrylate were dissolved in 200 ml of methanol in a three-neck flask and 1 g of $Li_2CO_3$ was added. The reaction mixture was heated for 6–8 h under reflux, cooled to 30° C. and 10 ml of aqueous HCl were added. The reaction mixture was stirred for 1 h, the methanol removed under reduced pressure and the product extracted with diethyl ether. The solvent was removed and methyl 4-trifluoronicotinate purified by vacuum distillation. 14 g (81%) of the product having a boiling point of 80° C./18 mbar were obtained.

$^1$H NMR ($CDCl_3$) δ: 9.17 (s, 1H), 8.97 (d, 1H, $^3J_{(H,H)}$=5 Hz), 7.71 (d,1H), 4.04 (s, 3H) ppm. $^{19}$F NMR δ:−62.4 (s, $CF_3$) ppm.

EXAMPLE 3
Methyl 4-trifluoromethylpyridine-3-carboxylate

Example 2 was repeated, except that, instead of $Li_2CO_3$, 1 g of $K_2CO_3$ was used. Yield 75%.

EXAMPLE 4
Methyl 4-trifluoromethylpyridine-3-carboxylate

Example 2 was repeated, except that, instead of $Li_2CO_3$, 1 g of sodium acetate was used. Yield 68%.

EXAMPLE 5
Methyl 4-hydroxy-6-methoxy-4-(trifluoromethyl)-1,4,5,6-tetrahydropyridine-3-carboxylate. (R and S) isomer 19 g (0.01 mol) of methyl 3-(4,4,4-trifluoro-3-oxo-1 butenylamino)acrylate were dissolved under $N_2$ in 200 ml of methanol in a three-neck flask and 2 g of $Li_2CO_3$ were added. The reaction mixture was stirred for 8 h at 50–60° C., the precipitate filtered off and the methanol substantially removed under reduced pressure. The two isomers were separated and purified by chromatography on $SiO_2$ (eluent ethyl acetate/heptane). Yield 88%.

Isomer 1. Yield 44%. M.P. 148–149° C.
$^1$H NMR ($CDCl_3$) (ABX Spin System) δ: 1.98 dm ($H_A$), $^2J_{(HaHb)}$=17 Hz; 2.68 dm ($H_B$), 3.39 (s, 3H, $OCH_3$), 3.73 (s, 3H, $OCH_3$), 4.57 m (1H), 5.6 bs (NH); 6.33 (1H, OH); 7.6 d (1H, CH,$^3$J=7 Hz) ppm. $^{19}$F NMR δ: −79.3 (s) ppm.
Isomer 2. Yield 43% (viscous oil). $^1$H NMR ($CDCl_3$) (ABX Spin System) δ: 1.97 ddkw ($H_A$), $^2J_{(HaHb)}$=16 Hz; 2.53 ddd ($H_B$)$^3$J=5.2, $^3$J=1.5 Hz, 3.42 (s, 3H, $OCH_3$), 3.71 (s, 3H, $OCH_3$), 4.57 dd (1H), 5.6 bs (NH); 6.6 (1H, OH); 7.6 d (1H, CH, $^3$J=7 Hz) ppm. $^{19}$F NMR δ: −81.0 (s) ppm.

The two products react with HCl at RT to give methyl 4-trifluoromethylpyridine-3-carboxylate. Yield 95%.

EXAMPLE 6 (Comparative)
Methyl 3-(4,4,4-trifluoro-3-oxo-1-butenylamino)acrylate Example 1 was repeated, except without reduced pressure.

Yield 77%, purity 95%.

EXAMPLE 7
Methyl 3-(4,4,4-trifluoro-3-oxo-1-butenylamino)acrylate

Example 1 was repeated, except that, instead of methyl 3,3-dimethoxypropionate, methyl 3-methoxyacrylate was used.

Yield 91%

What is claimed is:

1. A process for preparing a 4-haloalkylnicotinic ester of the formula (I),

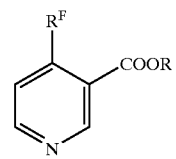

(I)

where
$R^F$ is $(C_1-C_4)$-haloalkyl and
R is $(C_{1-C6})$-alkyl;
which comprises
a) reacting an aminoketone of the formula (II), $$R^F\text{—}C(O)\text{—}CH\text{=}CH\text{—}NH_2 \quad (II)$$

in a condensation reaction under reduced pressure in the range from 5 to 150 mbar with a compound of the formulae (III) to (V), $$(R^1Z)CH\text{=}CH\text{—}COOR \quad (III),$$

$$(R^1Z)_2CH\text{—}CH_2\text{—}COOR \quad (IV),$$

$$HC\text{≡}C\text{—}COOR \quad (V),$$

where
$R^1$ is $(C_1-C_6)$-alkyl and
Z is O, S, $NR^1$ or C(O)O,
to give a compound of the formulae (VI) and/or (VII), $$R^F\text{—}(O)\text{—}CH\text{=}CH\text{—}NH\text{—}CH\text{=}CH\text{—}COOR \quad (VI)$$

$$R^F\text{—}C(O)\text{—}CH\text{=}CH\text{—}NH\text{—}CH(ZR^1)\text{—}CH_2\text{—}COOR \quad (VII)$$

b) and subjecting the reaction product to a ring closure reaction.

2. The process as claimed in claim 1, wherein, in the formulae (I)–(VII),
R is $CH_3$ and
R is $CF^3$.

3. The process as in claim 1, wherein step a) is carried out in the presence of a base selected from the group consisting of KO-t-butyl and NaOMe.

4. The process as claimed in claim 1, wherein step b) is carried out in the presence of an alkali metal carbonate and/or alkaline earth metal carbonate.

5. A process for preparing a compound of the formula (VI) and/or formula (VII), $$R^F\text{—}C(O)\text{—}CH\text{=}CH\text{—}NH\text{—}CH\text{=}CH\text{—}COOR \quad (VI)$$

$$R^F\text{—}C(O)\text{—}CH\text{=}CH\text{—}NH\text{—}CH(ZR^1)\text{—}CH_2\text{—}COOR \quad (VII)$$

where
$R^F$ is $(C_1-C_4)$-haloalkyl,
R, $R^1$ are identical or different $(C_1-C_6)$-alkyl and
Z is O, S, $NR^1$ or C(O)O, ps which comprises
reacting a 4-aminobutenone of the formula (II), $$R^F-C(O)-CH=CH-NH_2 \qquad (II)$$

in a condensation reaction under reduced pressure with a compound of the formulae (III) to (V), $$(R^1Z)CH=CH-COQR \qquad (III)$$

$$(R^1Z)_2CH-CH_2-COOR \qquad (IV)$$

$$HC\equiv C-COOR \qquad (V).$$

6. An intermediate of the formula:

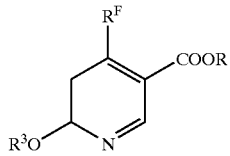

(XIII)

where
R is $(C_1-C_6)$-alkyl;
$R^F$ is $(C_1-C_4$-haloalkyl and
$R^3$ is $(C_1-C_6)$-alkyl.

7. The intermediate according to claim 6, wherein
R is $CH_3$,
$R^F$ is $CH_3$ and
$R^3$ is $CH^3$.

8. An intermediate of the formula:

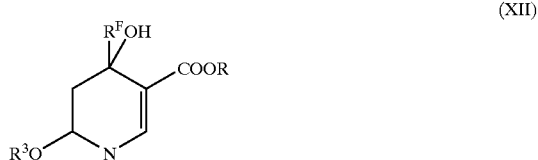

(XII)

where
R is $(C_1-C_6)$-alkyl;
$R^F$ is $(C_1-C_4)$-haloalkyl and
$R^3$ is $(C_1-C_6)$-alkyl.

9. The intermediate according to claim 8, wherein
R is $CH_3$,
$R^F$ is $CH_3$ and
$R^3$ is $CH_3$.

* * * * *